US011260017B2

(12) United States Patent
Motornov et al.

(10) Patent No.: US 11,260,017 B2
(45) Date of Patent: Mar. 1, 2022

(54) VOLUMIZING AND LENGTHENING EYELASH COATING COMPOSITIONS

(71) Applicant: L'ORÉAL, Paris (FR)

(72) Inventors: Mikhail Motornov, Clark, NJ (US); Angeles Fonolla-Moreno, Clark, NJ (US); Lilavati Patel, Edison, NJ (US)

(73) Assignee: L'ORÉAL, Paris (FR)

( * ) Notice: Subject to any disclaimer, the term of this patent is extended or adjusted under 35 U.S.C. 154(b) by 0 days.

(21) Appl. No.: 15/609,754

(22) Filed: May 31, 2017

(65) Prior Publication Data

US 2018/0344618 A1    Dec. 6, 2018

(51) Int. Cl.

| A61K 8/81 | (2006.01) |
| A61Q 1/10 | (2006.01) |
| A61K 8/06 | (2006.01) |
| A61K 8/46 | (2006.01) |
| A61K 8/37 | (2006.01) |
| A61K 8/31 | (2006.01) |
| A61K 8/41 | (2006.01) |
| A61K 8/86 | (2006.01) |

(52) U.S. Cl.
CPC ............ *A61K 8/8182* (2013.01); *A61K 8/062* (2013.01); *A61K 8/31* (2013.01); *A61K 8/37* (2013.01); *A61K 8/416* (2013.01); *A61K 8/463* (2013.01); *A61K 8/86* (2013.01); *A61Q 1/10* (2013.01); *A61K 2800/43* (2013.01); *A61K 2800/524* (2013.01); *A61K 2800/5426* (2013.01); *A61K 2800/594* (2013.01); *A61K 2800/83* (2013.01)

(58) Field of Classification Search
None
See application file for complete search history.

(56) References Cited

U.S. PATENT DOCUMENTS

| 5,161,555 | A |   | 11/1992 | Cansler et al. |  |
| 5,534,247 | A | * | 7/1996  | Franjac | A61K 8/06 |
|   |   |   |   |   | 132/218 |
| 9,072,686 | B2 |   | 7/2015  | Bui et al. |  |
| 2004/0013624 | A1 | * | 1/2004  | Mateu | A61K 8/922 |
|   |   |   |   |   | 424/70.7 |
| 2004/0091444 | A1 | * | 5/2004  | Loffler | A61K 8/8158 |
|   |   |   |   |   | 424/70.17 |
| 2006/0225616 | A1 | * | 10/2006 | Le Page | C09C 1/3669 |
|   |   |   |   |   | 106/499 |
| 2008/0145428 | A1 | * | 6/2008  | Zheng | A61K 8/87 |
|   |   |   |   |   | 424/487 |
| 2009/0142289 | A1 |   | 6/2009  | Arditty et al. |  |
| 2010/0055062 | A1 | * | 3/2010  | Arditty | A61K 8/06 |
|   |   |   |   |   | 424/70.7 |
| 2010/0089414 | A1 |   | 4/2010  | Wyatt et al. |  |
| 2011/0259355 | A1 | * | 10/2011 | Ybarra | A61K 8/817 |
|   |   |   |   |   | 132/203 |
| 2013/0039874 | A1 |   | 2/2013  | Li et al. |  |
| 2014/0286893 | A1 |   | 9/2014  | Alden-Danforth et al. |  |
| 2015/0007916 | A1 |   | 1/2015  | Oba et al. |  |
| 2015/0265507 | A1 |   | 9/2015  | Norman |  |
| 2015/0283062 | A1 |   | 10/2015 | Ilekti et al. |  |

FOREIGN PATENT DOCUMENTS

| EP | 1 462 023 A1 | 9/2004 |
| JP | 2007-175256 A | 7/2007 |
| WO | WO 2012/168894 A1 | 12/2012 |
| WO | WO 2013/163502 A1 | 10/2013 |

OTHER PUBLICATIONS

Aida (JP 2005145886) translation (Year: 2005).*
Ilekti et al. (FR 2996763) translation (Year: 2012).*
International Search Report dated Sep. 24, 2018 in PCT/US2018/035269, 6 pages.
Written Opinion of the International Searching Authority dated Sep. 24, 2018 in PCT/US2018/035269, 9 pages.

* cited by examiner

*Primary Examiner* — Quanglong N Truong
(74) *Attorney, Agent, or Firm* — Oblon, McClelland, Maier & Neustadt, L.L.P.

(57) ABSTRACT

The invention relates to an eyelash coating compositions comprising water, at least one polyelectrolytic compound, at least one film-forming agent, at least two waxes, and an emulsification system comprising low HLB emulsifier(s) (HLB value less than 8) and high HLB emulsifier(s) (HLB value greater than 16), as well as to methods of using such compositions.

21 Claims, No Drawings

VOLUMIZING AND LENGTHENING EYELASH COATING COMPOSITIONS

FIELD OF THE INVENTION

The present invention relates to eyelash coating compositions comprising water, at least one polyelectrolytic compound, at least one film-forming agent, at least two waxes, and an emulsification system comprising low HLB emulsifier(s) (HLB value less than 8) and high HLB emulsifier(s) (HLB value greater than 16). Preferably, the compositions further comprise at least one colorant.

DISCUSSION OF THE BACKGROUND

Many cosmetic compositions, including pigmented cosmetics such as foundations, concealers, lipsticks, and mascaras, and other cosmetic and sunscreen compositions, have been formulated in an attempt to impart desired cosmetic properties. For example, mascaras typically contain wax which is used to provide body and volume. However, the tackiness of the wax leads to mascara compositions that clump, apply unevenly, quickly dry the lashes, smudge, flake and are difficult to remove. Also, the tackiness of the wax limits the playtime (smoothness) of these waxes. When wax is eliminated from the mascaras, application and removal are facilitated, but the compositions lose desirable properties and tend to be runny.

Further, typically the addition of oils to traditional wax-containing mascara formulations (anhydrous or water-containing) can impact negatively the wear of the formula on the lashes, such that the mascara will smudge more.

There remains a need for improved cosmetic compositions having improved cosmetic properties, particularly mascaras and particularly water-containing mascaras, which are long-wearing, volumizing, lengthening, possess low flake properties and/or possess low smudging properties.

Accordingly, one aspect of the present invention is a water-containing care and/or makeup and/or treatment composition for keratinous material which has good cosmetic properties such as, for example, good long-wearing properties, good volumizing properties, good lengthening properties, low flaking properties and/or low smudging properties.

SUMMARY OF THE INVENTION

The present invention relates to compositions for keratinous material (for example, eyebrows and/or eyelashes) comprising water, at least one polyelectrolytic compound, at least one film-forming agent, at least two waxes, and an emulsification system comprising low HLB emulsifier(s) (HLB value less than 8) and high HLB emulsifier(s) (HLB value greater than 16). Preferably, the composition further comprises at least one coloring agent and/or is a mascara composition.

The present invention also relates to methods of treating, caring for and/or making up keratinous material (for example, eyebrows and/or eyelashes) by applying compositions of the present invention comprising water, at least one polyelectrolytic compound, at least one film-forming agent, at least two waxes, and an emulsification system comprising low HLB emulsifier(s) (HLB value less than 8) and high HLB emulsifier(s) (HLB value greater than 16), to the keratinous material in an amount sufficient to treat, care for and/or make up the keratinous material. Preferably, the composition further comprises at least one coloring agent and/or is a mascara composition.

The present invention also relates to methods of enhancing the appearance of keratinous material (for example, eyebrows and/or eyelashes) by applying compositions of the present invention comprising water, at least one polyelectrolytic compound, at least one film-forming agent, at least two waxes, and an emulsification system comprising low HLB emulsifier(s) (HLB value less than 8) and high HLB emulsifier(s) (HLB value greater than 16), to the keratinous material in an amount sufficient to enhance the appearance of the keratinous material. Preferably, the composition further comprises at least one coloring agent and/or is a mascara composition.

It is to be understood that both the foregoing general description and the following detailed description are exemplary and explanatory only, and are not restrictive of the invention.

DETAILED DESCRIPTION OF THE INVENTION

In the following description of the invention and the claims appended hereto, it is to be understood that the terms used have their ordinary and accustomed meanings in the art, unless otherwise specified.

"About" as used herein means within 10% of the indicated number (e.g. "about 10%" means 9%-11% and "about 2%" means 1.8%-2.2%).

"A" or "an" as used herein means "at least one."

As used herein, all ranges provided are meant to include every specific range within, and combination of subranges between, the given ranges. Thus, a range from 1-5, includes specifically 1, 2, 3, 4 and 5, as well as subranges such as and 2-5, 3-5, 2-3, 2-4, 1-4, etc.

"Film former", "film-forming polymer" or "film-forming agent" or "co-film former" as used herein means a polymer or resin that leaves a film on the substrate to which it is applied, for example, after a solvent accompanying the film former has evaporated, absorbed into and/or dissipated on the substrate.

"Wax" as used herein is a lipophilic fatty compound that is solid at ambient temperature (25° C.) and changes from the solid to the liquid state reversibly, having a melting temperature of more than 30° C. and, for example, more than 45° C., which can be as high as 150° C., and a hardness of more than 0.5 MPa at ambient temperature.

"Free" or "devoid" of as it is used herein means that while it is preferred that no amount of the specific component be present in the composition, it is possible to have very small amounts of it in the compositions of the invention provided that these amounts do not materially affect at least one, preferably most, of the advantageous properties of the compositions of the invention. Thus, for example, "free of solvents" means that non-aqueous solvents are preferably omitted (that is 0% by weight), but can be present in the composition at an amount of less than about 0.1% by weight, typically less than about 0.05% by weight, based on the total weight of the composition.

"Makeup Result" as used herein, refers to compositions where color remains the same or substantially the same as at the time of application, as viewed by the naked eye, after an extended period of time. "Makeup Result" may be evaluated by evaluating long wear properties by any method known in the art for evaluating such properties. For example, long wear may be evaluated by a test involving the application of a composition to keratin materials such as eyelashes and evaluating the color of the composition after an extended period of time. For example, the color of a composition may be evaluated immediately following application to keratin materials such as eyelashes and these characteristics may then be re-evaluated and compared after a certain amount of time. Further, these characteristics may be evaluated with respect to other compositions, such as commercially available compositions.

"Making up" as used herein means to provide decoration (for example, color) to keratin materials such as the eyelashes.

"Protecting" as used herein means to inhibit damage to keratin materials such as the eyelashes by providing a protective layer on the keratin materials.

"Substituted" as used herein, means comprising at least one substituent. Non-limiting examples of substituents for substitution include atoms, such as oxygen atoms and nitrogen atoms, as well as functional groups, such as hydroxyl groups, ether groups, alkoxy groups, acyloxyalkyl groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Water-resistance" as used herein, means resistance of a material (substance) to the penetration of water, which may cause degradation of that material. The method implemented if assessment of this invention is further disclosed.

"Transfer-resistance" as used herein refers to the quality exhibited by compositions that are not readily removed by contact with another material, such as, for example, a glass, an item of clothing or the skin, for example, when eating or drinking. Transfer resistance may be evaluated by any method known in the art for evaluating such. For example, transfer resistance of a composition may be evaluated by a "kiss" test. The "kiss" test may involve application of the composition to human keratin material such as hair, skin or lips followed by rubbing a material, for example, a sheet of paper, against the hair, skin or lips after expiration of a certain amount of time following application, such as 2 minutes after application. Similarly, transfer resistance of a composition may be evaluated by the amount of product transferred from a wearer to any other substrate, such as transfer from the hair, skin or lips of an individual to a collar when putting on clothing after the expiration of a certain amount of time following application of the composition to the hair, skin or lips. The amount of composition transferred to the substrate (e.g., collar, or paper) may then be evaluated and compared. For example, a composition may be transfer resistant if a majority of the product is left on the wearer's hair, skin or lips. Further, the amount transferred may be compared with that transferred by other compositions, such as commercially available compositions. In a preferred embodiment of the present invention, little or no composition is transferred to the substrate from the hair, skin or lips.

The compositions and methods of the present invention can comprise, consist of, or consist essentially of the essential elements and limitations of the invention described herein, as well as any additional or optional ingredients, components, or limitations described herein or otherwise useful.

Referred to herein are trade names for materials including, but not limited to polymers and optional components. The inventors herein do not intend to be limited by materials described and referenced by a certain trade name. Equivalent materials (e.g., those obtained from a different source under a different name or catalog (reference) number) to those referenced by trade name may be substituted and utilized in the methods described and claimed herein.

All percentages and ratios are calculated by weight unless otherwise indicated. All percentages are calculated based on the total weight of a composition unless otherwise indicated. All component or composition levels are in reference to the active level of that component or composition, and are exclusive of impurities, for example, residual solvents or by-products, which may be present in commercially available sources.

Water

According to present invention, compositions comprising water are provided. Preferably, compositions of the present invention comprise from about 5% to about 90% water, preferably from about 15% to about 80% water, preferably from about 20% to about 70% water, and preferably from about 30% to about 60% water by weight with respect to the total weight of the composition, including all ranges and subranges therebetween. Preferably, the compositions of the present invention are in the form of an emulsion, with a simple emulsion such as an oil-in-water (O/W) or wax-in-water being the most preferred form.

Polyelectrolytic Compound

According to present invention, compositions comprising at least one polyelectrolytic compound are provided. A "polyelectrolytic compound" is a polymer bearing electrolyte group(s) which dissociate in water, providing charge to the polymers. A polyelectrolytic compound can either be polycationic or polyanionic. Polycationic polyelectrolytic compounds are preferred in the compositions of the present invention.

According to preferred embodiments of the present invention, the at least one polyelectrolytic compound comprises at least one quaternary group. Suitable examples of acceptable polyelectrolytic compounds include, but are not limited to, Polyquaternium 2 (a polyelectrolyte formed from quaternized ioenes), Polyquaternium 4, Polyquaternium 5, Polyquaternium 6, Polyquaternium 7, Polyquaternium 8 (methyl and stearyl dimethylaminoethyl methacrylate quaternized with dimethylsulfate), Polyquaternium 10, Polyquaternium 11 (quaternized PVP and dimethylaminoethyl methacrylate), Polyquaternium 17 (polyelectrolyte formed from quaternized ioenes), Polyquaternium 18 (polyelectrolyte formed from quaternized ioenes), Polyquaternium 22, Polyquaternium 24 (polymeric quaternized ammonium salt of hydroxymethylcellulose and lauryl dimethyl ammonium substituted epoxide), Polyquaternium 27 (polyelectrolyte formed from quaternized ioenes), Polyquaternium 39, Polyquaternium 44, Polyquaternium 53, and Polyquaternium 67.

Preferably, the polyelectrolytic compound(s) is/are present in the compositions of the present invention in amounts of active material (e.g., solid content) generally ranging from about 0.05% to about 10%, preferably from about 0.1% to about 5%, and preferably from about 0.2% to about 1%, by weight, based on the total weight of the composition, including all ranges and subranges in between.

Film-Forming Agent

According to the present invention, compositions comprising at least one film-forming agent are provided. According to preferred embodiments, the compositions of the present invention comprise at least one dispersion of film forming particles in aqueous phase. The dispersion of film forming particles in aqueous phase is more generally known as latex.

Suitable polymers for the film-forming particles that may be used in the compositions of the present invention include, but are not limited to, synthetic polymers, free-radical type or polycondensate type polymers, polymers of natural origin, and mixtures thereof.

Preferably, the polymers for the film-forming particles may be selected from vinyl (co)polymers, (meth)acrylic (co)polymers, urethanes (co)polymers, and mixtures thereof. Advantageously, the polymer for the film-forming particles is selected from a styrene-(meth)acrylic and (meth) acrylic copolymer, a vinyl acetate and (meth)acrylic copolymer, and mixtures thereof.

Polymers for the film-forming particles of the free-radical type may be chosen, for example, from vinyl polymers or copolymers, such as acrylic polymers.

Vinyl film-forming polymers can result from the polymerization of monomers comprising at least one ethylenic unsaturation and at least one acidic group and/or esters of these acidic monomers and/or amides of these acidic monomers. Monomers comprising at least one acid group which may be used include, for example, $\alpha,\beta$-ethylenic unsaturated carboxylic acids such as acrylic acid, methacrylic acid, crotonic acid, maleic acid or itaconic acid. (Meth)acrylic acid and crotonic acid are, for example, used. Preferably, (meth)acrylic acid is used.

The esters of acidic monomers can be chosen, for example, from (meth)acrylic acid esters (also known as (meth)acrylates), such as (meth)acrylates of an alkyl, for example, a C1-C30 alkyl, such as a C1-C20 alkyl, (meth) acrylates of an aryl, such as a C6-C10 aryl, and (meth) acrylates of a hydroxyalkyl, such as a C2-C6 hydroxyalkyl. Among the alkyl (meth)acrylates that may be mentioned, examples include methyl methacrylate, ethyl methacrylate, butyl methacrylate, isobutyl methacrylate, 2-ethylhexyl methacrylate, lauryl methacrylate and cyclohexyl methacrylate. Among the hydroxyalkyl (meth)acrylates that may be mentioned, examples include hydroxyethyl acrylate, 2-hydroxypropyl acrylate, hydroxyethyl methacrylate and 2-hydroxypropyl methacrylate. Among the aryl (meth)acrylates that may be mentioned, examples include benzyl acrylate and phenyl acrylate. The (meth)acrylic acid esters that may be used are, for example, alkyl (meth)acrylates.

The alkyl group of the esters may be substituted. For example, the alkyl group of the esters may be either fluorinated or perfluorinated, i.e., some or all of the hydrogen atoms of the alkyl group are substituted with fluorine atoms. Further, examples of amides of the acid monomers that may be mentioned include (meth)acrylamides, such as N-alkyl (meth)acrylamides, for example, of a $C_2$-$C_{12}$ alkyl. Among the N-alkyl(meth)acrylamides that may be mentioned, examples include N-ethylacrylamide, N-t-butylacrylamide, N-t-octylacrylamide and N-undecylacrylamide.

The vinyl film-forming polymers may also result from the homopolymerization or copolymerization of monomers chosen from vinyl esters and styrene monomers. For example, these monomers may be polymerized with acid monomers and/or esters thereof and/or amides thereof, such as those mentioned above. Examples of vinyl esters that may be mentioned include vinyl acetate, vinyl neodecanoate, vinyl pivalate, vinyl benzoate and vinyl t-butylbenzoate. Styrene monomers that may be mentioned include styrene and $\alpha$-methylstyrene.

Among the film-forming polycondensates that may be mentioned, examples include polyurethanes, polyesters, polyesteramides, polyamides, epoxyester resins and polyureas, and modifications or derivatives of any of these.

The polyurethanes may be chosen from anionic, cationic, nonionic or amphoteric polyurethanes, polyurethane-acrylics, polyurethane-polyvinylpyrrolidones, polyester-polyurethanes, polyether-polyurethanes, polyureas and polyurea-polyurethanes, and mixtures thereof.

The polyesters may be obtained, in a known manner, by polycondensation of dicarboxylic acids with polyols, such as diols.

The dicarboxylic acid may be aliphatic, alicyclic or aromatic. Examples of such acids that may be mentioned include: oxalic acid, malonic acid, dimethylmalonic acid, succinic acid, glutaric acid, adipic acid, pimelic acid, 2,2-dimethylglutaric acid, azelaic acid, suberic acid, sebacic acid, fumaric acid, maleic acid, itaconic acid, phthalic acid, dodecanedioic acid, 1,3-cyclohexanedicarboxylic acid, 1,4-cyclohexanedicarboxylic acid, isophthalic acid, terephthalic acid, 2,5-norbornanedicarboxylic acid, diglycolic acid, thiodipropionic acid, 2,5-naphthalene-dicarboxylic acid and 2,6-naphthalenedicarboxylic acid. These dicarboxylic acid monomers may be used alone or as a combination of at least two dicarboxylic acid monomers. Among these monomers, phthalic acid, isophthalic acid and terephthalic acid may, for example, be used.

The diol may be chosen from aliphatic, alicyclic and aromatic diols. The diol used is, for example, chosen from ethylene glycol, diethylene glycol, triethylene glycol, 1,3-propanediol, cyclohexanedimethanol and 4-butanediol. Other polyols that may be used include glycerol, pentaerythritol, sorbitol and trimethylolpropane.

The polyesteramides may be obtained in a manner analogous to that of the polyesters, by polycondensation of diacids with diamines or amino alcohols. Diamines that may be used include, for example, ethylenediamine, hexamethylenediamine and meta- or para-phenylenediamine. An amino alcohol that may be used is, for example, monoethanolamine.

The polyester may also comprise at least one monomer bearing at least one —$SO_3M$ group, wherein M is chosen from a hydrogen atom, an ammonium ion $NH_4^+$ and a metal ion such as an $Na^+$, $Li^+$, $K^+$, $Mg^{2+}$, $Ca^{2+}$, $Cu^{2+}$, $Fe^{2+}$ or $Fe^{3+}$ ion. A difunctional aromatic monomer comprising such an —$SO_3M$ group may, for example, be used.

The aromatic nucleus of the difunctional aromatic monomer also comprising an —$SO_3M$ group as described above may be chosen, for example, from benzene, naphthalene, anthracene, biphenyl, oxybiphenyl, sulfonylbiphenyl and methylenebiphenyl nuclei. Among the difunctional aromatic monomers also comprising an —$SO_3M$ group, mention may be made, for example, of sulfoisophthalic acid, sulfoterephthalic acid, sulfophthalic acid, 4-sulfonaphthalene-2,7-dicarboxylic acid.

The copolymers used are, for example, those based on isophthalate/sulfoisophthalate, such as copolymers obtained by condensation of diethylene glycol, cyclohexanedimethanol, isophthalic acid and sulfoisophthalic acid.

The polymer for the film forming particles may also be a liposoluble polymer. Examples of the liposoluble polymer that may be mentioned include copolymers of a vinyl ester (wherein the vinyl group is directly linked to the oxygen atom of the ester group and the vinyl ester comprises a radical chosen from saturated, linear or branched hydrocarbon-based radicals of 1 to 19 carbon atoms, linked to the carbonyl of the ester group) and of at least one other monomer, which may be a vinyl ester (different from the vinyl ester already present), an $\alpha$-olefin (comprising from 8 to 28 carbon atoms), an alkyl vinyl ether (the alkyl group of which comprises from 2 to 18 carbon atoms) or an allylic or methallylic ester (comprising a radical chosen from saturated, linear or branched hydrocarbon-based radicals of 1 to 19 carbon atoms, linked to the carbonyl of the ester group).

These copolymers may be crosslinked using crosslinking agents that may be either of the vinylic type or of the allylic or methallylic type, such as tetraallyloxyethane, divinylbenzene, divinyl octanedioate, divinyl dodecanedioate and divinyl octadecanedioate.

Examples of these copolymers which may be mentioned include the following copolymers: vinyl acetate/allyl stearate, vinyl acetate/vinyl laurate, vinyl acetate/vinyl stearate, vinyl acetate/octadecene, vinyl acetate/octadecyl vinyl ether, vinyl propionate/allyl laurate, vinyl propionate/vinyl laurate, vinyl stearate/1-octadecene, vinyl acetate/1-dodecene, vinyl stearate/ethyl vinyl ether, vinyl propionate/cetyl vinyl ether, vinyl stearate/allyl acetate, vinyl 2,2-dimethyloctanoate/vinyl laurate, allyl 2,2-dimethylpentanoate/vinyl laurate, vinyl dimethylpropionate/vinyl stearate, allyl dimethylpropionate/vinyl stearate, vinyl propionate/vinyl stearate, crosslinked with 0.2% divinylbenzene, vinyl dimethylpropionate/vinyl laurate, crosslinked with 0.2% divinylbenzene, vinyl acetate/octadecyl vinyl ether, crosslinked with 0.2% tetraallyloxyethane, vinyl acetate/allyl stearate, crosslinked with 0.2% divinylbenzene, vinyl acetate/1-octadecene, crosslinked with 0.2% divinylbenzene, and allyl propionate/allyl stearate, crosslinked with 0.2% divinylbenzene.

Further examples of the liposoluble film-forming polymers include liposoluble copolymers, such as those resulting from the copolymerization of vinyl esters comprising from 9 to 22 carbon atoms or of alkyl acrylates or methacrylates, wherein the alkyl radicals comprise from 10 to 20 carbon atoms. Such liposoluble copolymers may be chosen, for example, from polyvinyl stearate, polyvinyl stearate crosslinked with the aid of divinylbenzene, of diallyl ether or of diallyl phthalate copolymers, polystearyl (meth)acrylate, polyvinyl laurate and polylauryl (meth)acrylate copolymers, it being possible for these poly(meth)acrylates to be crosslinked with the aid of ethylene glycol dimethacrylate or tetraethylene glycol dimethacrylate. The liposoluble copolymers described above are known and are described, for example, in French patent application FR-A-2 232 303; they may have a weight-average molecular weight ranging, for example, from 2,000 to 500,000 such as from 4,000 to 200,000.

Among the liposoluble film-forming polymers which may be used herein, mention may also be made, for example, of polyalkylenes such as copolymers of $C_2$-$C_{20}$ alkenes, such as polybutene, alkylcelluloses with a linear or branched, saturated or unsaturated $C_1$-$C_8$ alkyl radical, for instance ethylcellulose and propylcellulose, copolymers of vinylpyrrolidone (VP) such as copolymers of vinylpyrrolidone and of $C_2$-$C_{40}$ alkene such as $C_3$-$C_{20}$ alkene. Among the VP copolymers which may be used herein, mention may be made, for example, of the copolymers of VP/vinyl acetate, VP/ethyl methacrylate, butylated polyvinylpyrrolidone (PVP), VP/ethyl methacrylate/methacrylic acid, VP/eicosene, VP/hexadecene, VP/triacontene, VP/styrene or VP/acrylic acid/lauryl methacrylate.

Specific examples of aqueous dispersions of film-forming particles which may be used are the acrylic dispersions sold under the names "Neocryl XK-90®", "Neocryl A-1070®", "Neocryl A-1090®", "Neocryl BT-62®", "Neocryl A-1079®" and "Neocryl A-523®" by the company Avecia-Neoresins, "Dow Latex 432®" by the company Dow Chemical, "Daitosol 5000 AD®" or "Daitosol 5000 SJ" by the company Daito Kasey Kogyo; the aqueous dispersions of polyurethane sold under the names "Neorez R-981®" and "Neorez R-974®" by the company Avecia-Neoresins, "Avalure UR-405®", "Avalure UR-410®", "Avalure UR-425®", "Avalure UR-450®", "Sancure 875®", "Sancure 861®", "Sancure 878®" and "Sancure 2060®" by the company Goodrich, "Impranil 85®" by the company Bayer and "Aquamere H-151®" by the company Hydromer; vinyl dispersions, for instance "Mexomer PAM" and also acrylic dispersions in isododecane, for instance "Mexomer PAP" by the company Chimex.

Further specific examples of latex polymers for use in the present invention further include ethylhexyl acrylate/hema copolymer (and) acrylates/diethylaminoethyl methacrylate/ethylhexyl acrylate copolymer (Syntran®PC 5775), styrene/acrylates/ammonium methacrylate copolymer (Syntran®5760, Syntran®5009, Syntran®PC5620), polyacrylate-21 (and) acrylates/dimethylaminoethyl methacrylate copolymer (Syntran®PC5100, Syntran®PC5776, Eudragit®E 100, Jurymer ET-410C), styrene/acrylates/ammonium methacrylate copolymer (Syntran®5009 CG), olefin/acrylate grafted polymer (and) sodium laureth sulfate (and C12-15 SEC-pareth 15 (Syntran®EX108), acrylates copolymer (Aculyn®33A Polymer, Avalure®Ace 210/120/315 Acrylic Copolymer, Carbopol® Aqua SF-1 Polymer, Coatex®Co 633, Eliclear®380/700/4U, Eudragit® L 100, Joncryl®85, Luviflex®Soft), acrylates/ethylhexyl acrylate copolymer. The Syntran® polymers are commercially available from the supplier Interpolymer Corp.

According to preferred embodiments, compositions of the present invention may comprise instead of, or in addition to, the dispersion of film forming particles in aqueous phase discussed above one or more film-forming agents suitable for use in compositions for application to eyebrows and/or eyelashes. Such film-forming agents can be, for example, water-soluble or liposoluble. Acceptable film-forming are known in the art and include, but are not limited to, those disclosed in U.S. patent application publication no. 2004/0170586, the entire contents of which is hereby incorporated by reference.

Specific examples of film-forming agents include, but are not limited to, proteins, such as proteins of plant origin, such as, for example, wheat or soya proteins; or proteins of animal origin, such as keratins, for example keratin hydrolysates and sulfonic keratins; cellulose polymers, such as, for example, hydroxyethylcellulose, hydroxypropylcellulose, methylcellulose or ethylhydroxyethylcellulose; gums arabic, guar gum, xanthan derivatives or karaya gum; alginates and carrageenans; glycoaminoglycans, hyaluronic acid and its derivatives; shellac resin, gum sandarac, dammars, elemis or copals; muccopolysaccharides, such as chondroitin sulfates, and mixtures thereof.

Specific examples of suitable film-forming agents also include silicone resins such as, for example, MQ resins (for example, trimethylsiloxysilicates), T-propyl silsesquioxanes and MK resins (for example, polymethylsilsesquioxanes), silicone esters such as those disclosed in U.S. Pat. Nos. 6,045,782, 5,334,737, and 4,725,658, the disclosures of which are hereby incorporated by reference, polymers comprising a backbone chosen from vinyl polymers, methacrylic polymers, and acrylic polymers and at least one chain chosen from pendant siloxane groups and pendant fluorochemical groups such as those disclosed in U.S. Pat. Nos. 5,209,924, 4,693,935, 4,981,903, 4,981,902, and 4,972,037, and WO 01/32737, the disclosures of which are hereby incorporated by reference, polymers such as those described in U.S. Pat. No. 5,468,477, the disclosure of which is hereby incorporated by reference (a non-limiting example of such polymers is poly(dimethylsiloxane)-g-poly(isobutyl methacrylate), which is commercially available from 3M Company under the tradename VS 70 IBM), and mixtures thereof.

Specific examples of suitable polymers further include, but are not limited to, polyalkylenes, polyvinylpyrrolidone (PVP) or vinylpyrrolidone (VP) homopolymers or copolymers, copolymers of a $C_2$ to $C_{30}$, such as $C_3$ to $C_{22}$ alkene, and combinations thereof. As specific examples of VP copolymers which can be used in the invention, mention may be made of VP/vinyl acetate, VP/ethyl methacrylate, butylated polyvinylpyrrolidone (PVP), VP/ethyl methacrylate/methacrylic acid, VP/eicosene, VP/hexadecene, VP/triacontene, VP/styrene or VP/acrylic acid/lauryl methacrylate copolymer, and mixtures thereof.

Preferably, the film-forming polymers are present in the compositions of the present invention in an amount sufficient to form a film upon a substrate to which it has been applied (for example, eyebrows and/or eyelashes).

So, for example, when film-forming particles are present in the composition and are in the form of a commercial product containing the film-forming particles in aqueous dispersion, the amount of active material (that is, film-forming particles) within the aqueous dispersion is sufficient to form a film upon a substrate to which it has been applied.

Preferably, the film-forming polymer(s) is/are present in the compositions of the present invention in amounts of active material (e.g., solid content) generally ranging from about 0.5% to about 40%, preferably from about 2% to about 20%, and preferably from about 5% to about 10%, by weight, based on the total weight of the composition, including all ranges and subranges in between.

Preferably, the polyelectrolytic compound(s) and film-forming polymer(s) are present in the compositions of the present invention in weight ratios (solid content) of polyelectrolytic compound(s) to film forming polymer(s) of from 0.55:0.5 polyelectrolytic compound(s) to 10:40 film forming polymer(s), preferably from 0.1:2 polyelectrolytic compound(s) to 5:20 film forming polymer(s), and preferably from 0.2:5 polyelectrolytic compound(s) to 1:10 film forming polymer(s), including all ranges and subranges therebetween.

Emulsification System

According to the present invention, compositions comprising an emulsification system comprising at least one low HLB emulsifier(s) (HLB value less than 8) and at least one high HLB emulsifier(s) (HLB value greater than 16), are provided.

According to preferred embodiments, the low HLB emulsifier is selected from the group consisting of ionic emulsifiers, nonionic emulsifiers, and mixtures thereof.

According to preferred embodiments, the high HLB emulsifier is selected from the group consisting of ionic emulsifiers, nonionic emulsifiers, and mixtures thereof.

"HLB" refers to the "hydrophilic-lipophilic balance" associated with emulsifiers. In particular, "HLB" value relates to the ratio of hydrophilic groups and lipophilic groups in emulsifiers, and also relates to solubility of the emulsifiers. Lower HLB emulsifiers are more soluble in oils (lipophilic material) and are more appropriate for use in water-in-oil (W/O) emulsions. Higher HLB emulsifiers are more soluble in water (hydrophilic material) and are more appropriate for oil-in-water (O/W) emulsions.

By way of example, the following emulsifiers have been reported to have the following HLB values:

Propylene Glycol Isostearate HLB=2.5;
Glyceryl Stearate HLB=3.8;
Sorbitan Isostearate HLB=4.7;
Oleth-2 HLB=4.9;
Glyceryl Laurate HLB=5.2;
Ceteth-2 HLB=5.3;
Methyl Glucose Sesquistearate HLB=6.6;
Ceteth-30 HLB=16.5;
C12-13 pareth-23 HLB=16.7;
Polysorbate 20 HLB=16.7;
Laureth-23 HLB=16.9;
PEG-100 Stearate HLB=18.8; and
Sodium lauryl sulfate HLB=40.

According to preferred embodiments, one or more of the emulsifiers is a fatty alcohol, a fatty acid, or ester thereof, optionally alkoxylated (ethoxylated, propoxylated, etc.) and/or pegylated. Fatty acids correspond the formula R—COOH and fatty alcohols correspond to the formula R—OH, in which R denotes a saturated or unsaturated hydrocarbon radical preferably having from 7 to 45 carbon atoms, preferably from 9 to 35 carbon atoms, preferably from 15 to 35 carbon atoms, preferably from 15 to 21 carbon atoms, and preferably from 16 to 18 carbon atoms. Mention may be made of, for example, lauric acid/alcohol, stearic acid/alcohol, oleic acid/alcohol, behenyl acid/alcohol, cetyl acid/alcohol and mixtures thereof (including ceteareth compounds).

Suitable emulsifiers include ethoxylated fatty alcohols, ethoxylated fatty acids, partial glycerides of ethoxylated fatty acids, polyglycerolated fatty acid triglycerides and ethoxylated derivatives thereof, and mixtures thereof.

Suitable alkoxylated fatty alcohols include, for example, the addition products of ethylene oxide with lauryl alcohol, in particular those containing from 9 to 250 oxyethylenated groups (having CTFA names Laureth-9 to Laureth-50); the addition products of ethylene oxide with behenyl alcohol, in particular those containing from 9 to 250 oxyethylenated groups (having CTFA names Beheneth-9 to Beheneth-50); the addition products of ethylene oxide with cetearyl alcohol (mixture of cetyl alcohol and of stearyl alcohol) in particular those containing from 9 to 250 oxyethylenated groups (having CTFA names Ceteareth-9 to Ceteareth-33); the addition products of ethylene oxide with cetyl alcohol, in particular those containing from 9 to 250 oxyethylenated groups (having CTFA names Ceteth-9 to Ceteth-30); the addition products of ethylene oxide with stearyl alcohol, in particular those containing from 9 to 30 oxyethylenated groups (having CTFA names Steareth-9 to Steareth-30; the addition products of ethylene oxide with isostearyl alcohol, in particular those containing from 9 to 250 oxyethylenated groups (having CTFA names Isosteareth-9 to Isosteareth-50); and mixtures thereof, wherein the amount of alkoxylation preferably ranges from 9 to 250, and preferably from 25 to 200, including all ranges and subranges therebetween including, for example, 30 to 200, 50 to 100, etc.

Suitable alkoxylated fatty acid include, for example, the addition products of ethylene oxide with lauric acid, palmitic acid, stearic acid or behenic acid, and mixtures thereof, in particular those containing from 9 to 250 oxyethylenated groups, such as laurates of PEG-9 to PEG-50 (having CTFA names: PEG-9 laurate to PEG-50 laurate); palmitates of PEG-9 to PEG-50 (having CTFA names: PEG-9 palmitate to PEG-50 palmitate); stearates of PEG-9 to PEG-250 (having CTFA names: PEG-9 stearate to PEG-250 stearate such as PEG-100 stearate to PEG-200 stearate); palmitostearates of PEG-9 to PEG-50; behenates of PEG-9 to PEG-50 (having CTFA names: PEG-9 behenate to PEG-50 behenate); and mixtures thereof, wherein the amount of alkoxylation preferably ranges from 9 to 250, and preferably from 50 to 200, including all ranges and subranges therebetween including, for example, 100 to 200, 50 to 100, etc.

Preferably, about 0.1% to about 15% of low HLB emulsifier(s) (HLB value less than 8), and about 0.1% to about 15% of high HLB emulsifier(s) (HLB value greater than 16) by weight are present in the compositions of the present invention, based on the total weight of the composition; preferably, about 0.1% to about 10% of low HLB emulsifier(s) (HLB value less than 8), and about 0.1% to about 12.5% of high HLB emulsifier(s) (HLB value greater than 16) by weight are present in the compositions of the present invention, based on the total weight of the composition; and preferably, about 0.1% to about 7% of low HLB emulsifier(s) (HLB value less than 8), and about 0.2% to about 10% of high HLB emulsifier(s) (HLB value greater than 16) by weight are present in the compositions of the present invention, based on the total weight of the composition, including all ranges and subranges in between.

Preferably, low HLB emulsifier(s) and high HLB emulsifier(s) are present in the compositions of the present invention in weight ratios of low HLB surfactant to high HLB surfactant of from 0.5:10 low HLB surfactant to 0.5:15 high HLB surfactant, and preferably from 0.7:5 low HLB surfactant to 1:9 high HLB surfactant, including all ranges and subranges therebetween.

Waxes

According to the present invention, compositions comprising at least two waxes are provided. Each or all of the waxes can be hydrocarbon, fluorinated and/or silicone, and be of plant, mineral, animal and/or synthetic origin.

Suitable examples of waxes that can be used in accordance with the present disclosure include those generally used in the cosmetics field: they include those of natural origin, such as beeswax, carnauba wax, candelilla wax, ouricoury wax, Japan wax, cork fibre wax or sugar cane wax, rice wax, montan wax, paraffin wax, lignite wax or microcrystalline wax, ceresin or ozokerite, and hydrogenated oils such as hydrogenated castor oil or jojoba oil; synthetic waxes such as the polyethylene waxes obtained from the polymerization or copolymerization of ethylene, and Fischer-Tropsch waxes, or else esters of fatty acids, such as octacosanyl stearate, glycerides which are concrete at 30° C., for example at 45° C., silicone waxes, such as alkyl- or alkoxydimethicones having an alkyl or alkoxy chain ranging from 10 to 45 carbon atoms, poly(di)methylsiloxane esters which are solid at 30° C. and whose ester chain comprising at least 10 carbon atoms, or else di(1,1,1-trimethylolpropane) tetrastearate, which is sold or manufactured by Heterene under the name HEST 2T-4S, and mixtures thereof.

Further suitable examples of wax include, but are not limited to, BIS-PEG-12 DIMETHICONE CANDELILLATE wax such as for example the Siliconyl Candelilla Wax marketed by the company KOSTER KEUNEN, hydrogenated Jojoba wax such as for example that marketed by the company DESERT WHALE, hydrogenated palm oil such as that marketed by the company SIO, rice bran wax, Sumac wax, ceresin waxes, laurel wax, Chinese insect wax, Shellac wax, hydrogenated olive oil such as Waxolive from the company SOLIANCE, waxes obtained by hydrogenation of olive oil esterified with C12 to C18 chain fatty alcohols such as those sold by the company SOPHIM under the brand names Phytowax Olive 12L44, 14L48, 16L55 and 18L57, waxes obtained by hydrogenation of castor oil esterified with cetyl or behenyl alcohol such as for example those which are sold under the names Phytowax Ricin 16 L 64 and Phytowax Ricin 22 L 73 by the company SOPHIM, hydrogenated Cameline wax, Ouricury wax, Montan wax, ozokerite waxes such as for example Wax SP 1020 P marketed by the company Strahl & Pitsch, microcrystalline waxes such as for example that sold under the brand name Microwax HW by the company PARAMELT, triglycerides of lauric, palmitic, cetylic and stearic acids (INCI name: hydrogenated coco glycerides) such as for example that sold under the brand name Softisan 100 by the company SASOL, polymethylene waxes such as for example that sold under the brand name Cirebelle 303 by the company SASOL, polyethylene waxes such as for example those sold under the brand names Performalene 400 polyethylene, Performalene 655 polyethylene and Performalene 500-L polyethylene by the company New Phase Technologies, alcohol-polyethylene waxes such as for example that marketed under the name Performacol 425 Alcohol by the company BARECO, the 95/5 ethylene/acrylic acid copolymer sold under the brand name AC 540 wax by the company Honeywell, hydroxyoctacosanyl hydroxy-stearate such as for example that sold under the brand name Elfacos C 26 by the company AKZO, octacosanyl stearate such as for example that marketed under the name Kester Wax K 82H by the company KOSTER KEUNEN, stearyl stearate such as for example that marketed under the name Liponate SS by the company LIPO CHEMICALS, pentaerythritol distearate such as for example that marketed under the name Cutina PES by the company COGNIS, the mixture of dibehenyl adipate, dioctadecyl adipate and di-eicosanyl adipate (INCI name C18-C22 dialkyl adipate), the mixture of dilauryl adipate and ditetradecyl adipate (INCI name: C12-C14 dialkyl adipate), the mixture of dioctadecyl sebacate, didocosyl sebacate and dieicosyl sebacate (INCI name: C18-C22 dialkyl sebacate) and the mixture of dioctadecyl octadecanedioate, didocosyl octanedioate and dieicosyl octanedioate (INCI name: C18-C22 dialkyl octanedioate) such as for example those marketed by the company COGNIS, pentaerythrityl tetrastearate such as for example Liponate PS-4 from the company Lipo Chemicals, tetracontanyl stearate such as for example Kester Wax K76H from the company KOSTER KEUNEN, stearyl benzoate such as for example Finsolv 116 from the company FINETEX, behenyl fumarate such as for example Marrix 222 from the company AKZO BERNEL, di-(trimethylol-1,1,1-propane) tetrastearate such as for example that which is offered under the name "HEST 2T-4S" by the company HETERENE, didotriacontanyl distearate such as for example Kester Wax K82D from the company KOSTER KEUNEN, polyethylene glycol montanate with 4 ethylene oxide units (PEG-4) such as for example that which is sold under the brand name Clariant Licowax KST1, hexanediol disalicylate such as for example Betawax RX-13750 marketed by the company CP Hall, dipentaerythritol hexastearate such as for example that which is sold under the brand name Hest 2P-6S by the company HETERENE, ditrimethylolpropane tetrabehenate such as for example that which is sold under the brand name Hest 2T-4B by the company HETERENE, Jojoba esters such as for example that which is sold under the brand name Floraester HIP by the company FLORATECH, mixtures of linear (C20-40) carboxylic acid/saturated hydrocarbons (INCI name: C20-40 acid polyethylene) such as for example Performacid 350 acid from the company NEW PHASE TECHNOLOGIES, synthetic wax of the Fischer-Tropsch type such as that marketed under the name Rosswax 100 by the company ROSS, cetyl alcohol, stearyl alcohol, behenyl alcohol, dioctadecyl carbonate such as for example Cutina KE 3737, saccharose polybehenate such as for example Crodaderm B from the company CRODA, waxes of plant origin such as carnauba wax, candelilla wax, hydrogenated jojoba wax, sumac wax, waxes obtained by hydrogenation of olive oil esterified with C12 to C18 chain fatty alcohols sold by the company SOPHIM in the Phytowax range (12L44, 14L48, 16L55 and 18L57), rice bran wax, cetyl, stearyl and behenyl alcohols, laurel wax, Ouricury wax and mixtures thereof can be mentioned.

According to preferred embodiments, compositions of the present invention comprise a lanolin compound, either of plant origin or of synthetic origin. Suitable examples of lanolin compounds include, but are not limited to, lanolin of plant origin and derivative or modified compounds obtained by synthesis from starting materials of plant origin, preferably ethers or ester compounds. Preferred ethers are liposoluble polyethers resulting from the polyetherification between one or more $C_2$-$C_{100}$ and preferably $C_2$-$C_{50}$ diols. Preferred esters are esters of a glycerol oligomer, especially diglycerol esters, in particular condensates of adipic acid and of glycerol, for which some of the hydroxyl groups of the glycerols have reacted with a mixture of fatty acids such as stearic acid, capric acid, stearic acid and isostearic acid, and 12-hydroxystearic acid, especially such as the product sold under the brand name Softisan 649 by the company Sasol, arachidyl propionate sold under the brand name Waxenol 801 by Alzo, phytosterol esters, fatty acid triglycerides and derivatives thereof, pentaerythritol esters, on-crosslinked polyesters resulting from polycondensation between a linear or branched C4-C50 dicarboxylic acid or polycarboxylic acid and a C2-C50 diol or polyol, aliphatic esters of an ester resulting from the esterification of an aliphatic hydroxycarboxylic acid with an aliphatic carboxylic acid, polyesters resulting from the esterification, with a polycarboxylic acid, of an ester of an aliphatic hydroxycarboxylic acid, the said ester comprising at least two hydroxyl groups, such as the products Risocast DA-H® and Risocast DA-L®, esters of a diol dimer and of a diacid dimer, where appropriate esterified on their free alcohol or acid function(s) with acid or alcohol radicals, such as Plandool-G, and mixtures thereof.

According to preferred embodiments, at least one wax is a low melting point wax having a melting point below 70° C. (for example, paraffin wax) and at least one wax is a high melting point wax having a melting point above 70° C. (for example, rice bran wax) in the compositions of the present invention. According to these embodiments, preferably, low melting point wax(es) and high melting point wax(es) are present in the compositions of the present invention in a weight ratio of from 0.5:40, preferably from 5:32, and preferably from 10:27, including all ranges and subranges therebetween.

Preferably, the waxes are present in a total amount ranging from about 1% to about 45% by weight, preferably from about 7% to about 34% by weight, and preferably from about 9% to about 29% by weight, based on the total weight of the composition, including all ranges and subranges within these ranges.

Oil Phase

According to embodiments of the present invention, the compositions of the present invention may optionally further comprise at least one oil. "Oil" means any non-aqueous medium which is liquid at ambient temperature (25° C.) and atmospheric pressure (760 mm Hg).

Suitable oils include volatile silicone oils. Examples of such volatile silicone oils include linear or cyclic silicone oils having a viscosity at room temperature less than or equal to 6 cSt and having from 2 to 7 silicon atoms, these silicones being optionally substituted with alkyl or alkoxy groups of 1 to 10 carbon atoms. Specific oils that may be used in the invention include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96A of 6 cSt viscosity, a commercial product from Shin Etsu having a flash point of 94° C. Preferably, the volatile silicone oils have a flash point of at least 40° C.

Suitable oils include non-silicone volatile oils and may be selected from volatile hydrocarbon oils, volatile esters and volatile ethers. Examples of such volatile non-silicone oils include, but are not limited to, volatile hydrocarbon oils having from 8 to 16 carbon atoms and their mixtures and in particular branched $C_8$ to $C_{16}$ alkanes such as $C_8$ to $C_{16}$ isoalkanes (also known as isoparaffins), isododecane, isodecane, and for example, the oils sold under the trade names of Isopar or Permethyl. Preferably, the volatile non-silicone oils have a flash point of at least 40° C.

Suitable oils include synthetic oils or esters of formula $R_5COOR_6$ in which $R_5$ represents a linear or branched higher fatty acid residue containing from 1 to 40 carbon atoms, including from 7 to 19 carbon atoms, and $R_6$ represents a branched hydrocarbon-based chain containing from 1 to 40 carbon atoms, including from 3 to 20 carbon atoms, with $R_6+R_7 \geq 10$, such as, for example, Purcellin oil (cetostearyl octanoate), isononyl isononanoate, $C_{12}$ to $C_{15}$ alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; pentaerythritol esters; and synthetic ethers containing from 10 to 40 carbon atoms.

If present, the oil(s) is/are present in the compositions of the present invention in an amount ranging from about 0.1% to about 20% by weight, more preferably from about 0.4% to about 15% by weight, and preferably from about 0.5% to about 10% by weight, based on the total weight of the composition, including all ranges and subranges within these ranges.

Coloring Agents

According to preferred embodiments of the present invention, compositions optionally further comprising at least one coloring agent are provided. Preferably, such colored compositions can be cosmetic compositions such as mascaras.

According to this embodiment, the at least one coloring agent is preferably chosen from pigments, dyes, such as liposoluble dyes, nacreous pigments, and pearling agents.

Representative liposoluble dyes which may be used according to the present invention include Sudan Red, DC Red 17, DC Green 6, ß-carotene, soybean oil, Sudan Brown, DC Yellow 11, DC Violet 2, DC Orange 5, annatto, and quinoline yellow. The liposoluble dyes, when present, generally have a concentration ranging up to 20% by weight of the total weight of the composition, such as from 0.0001% to 6%, including all ranges and subranges therebetween.

The nacreous pigments which may be used according to the present invention may be chosen from white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride. The nacreous pigments, if present, may be present in the composition in a concentration ranging up to 50% by weight of the total weight of the composition, such as from 0.1% to 20%, preferably from 0.1% to 15%, including all ranges and subranges therebetween.

The pigments, which may be used according to the present invention, may be chosen from white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, and ferric blue. Representative examples of organic pigments include carbon black, pigments of D & C type, and lakes based on cochineal carmine, barium, strontium, calcium, and aluminum.

If present, the pigments may be present in the composition in a concentration ranging up to 50% by weight of the total weight of the composition, such as from 0.5% to 40%, and further such as from 2% to 30%, including all ranges and subranges therebetween. In the case of certain products, the pigments, including nacreous pigments, may, for example, represent up to 50% by weight of the composition.

Volumizing Agent

According to the present invention, compositions optionally further comprising at least one volumizing agent are provided. Suitable examples of acceptable volumizing agents include, but are not limited to, inert fillers.

Any suitable inert filler may be used in accordance with the present invention. The term "inert filler" means any particle that is solid at room temperature and atmospheric pressure which does not react chemically with the various ingredients of the composition and which is insoluble in these ingredients.

The at least one inert filler preferably has a melting point which is greater than 150° C., preferably greater than 170° C., preferably greater than 200° C., preferably greater than 250° C., and preferably greater than 300° C.

The at least one inert filler may or may not be absorbent, i.e., capable in particular of absorbing the oils of the composition.

The at least one inert filler may have an apparent diameter ranging from 0.01 µm to 150 µm, preferably from 0.1 µm to 120 µm, preferably from 0.5 µm to 80 µm, preferably from 0.75 µm to 40 µm, and preferably from 1 µm to 10 µm, including all ranges and subranges therebetween. An apparent diameter corresponds to the diameter of the circle into which the elementary particle fits along its shortest dimension (thickness for leaflets).

The at least one inert filler may be mineral or organic, and lamellar, spherical or oblong. The at least one inert filler may be chosen from talc, mica, silica, kaolin, polyamide powders such as Nylon® powder, poly-β-alanine powder, polyethylene powder, acrylic polymer powder and in particular polymethyl methacrylate (PMMA) powder, for instance the product sold or made by Wacker under the reference Covabead LH-85 (particle size 10-12 µm) or acrylic acid copolymer powder (Polytrap® from Dow Corning), polytetrafluoroethylene (Teflon®) powders, lauroyllysine, boron nitride, starch, hollow polymer microspheres such as those of polyvinylidene chloride/acrylonitrile, for instance Expancel® (Nobel Industrie), hollow polymer microspheres (Tospearl® from Toshiba, for example), precipitated calcium carbonate, magnesium carbonate and hydrocarbonate, hydroxyapatite, hollow silica microspheres, glass or ceramic microcapsules and polyester particles.

Preferably, when the volumizing agent(s) is/are inert filler(s), the volumizing agent(s) is/are present the compositions of the present invention in amounts of active material generally ranging from about 0.5% to about 20%, preferably from about 1% to about 15%, and preferably from about 2% to about 10%, by weight, based on the total weight of the composition, including all ranges and subranges in between.

Additional Additives

The composition of the invention can also comprise any additive usually used in the field under consideration. For example, dispersants such as poly(12-hydroxystearic acid), antioxidants, film forming agents, essential oils, sunscreens, preserving agents, fragrances, fillers, neutralizing agents, cosmetic and dermatological active agents such as, for example, emollients, moisturizers, vitamins, essential fatty acids, surfactants, silicone elastomers, pasty compounds, and mixtures thereof can be added. A non-exhaustive listing of such ingredients can be found in U.S. patent application publication no. 2004/0170586, the entire contents of which is hereby incorporated by reference. Further examples of suitable additional components can be found in the other references which have been incorporated by reference in this application. Still further examples of such additional ingredients may be found in the *International Cosmetic Ingredient Dictionary and Handbook* ($9^{th}$ ed. 2002).

A person skilled in the art will take care to select the optional additional additives and/or the amount thereof such that the advantageous properties of the composition according to the invention are not, or are not substantially, adversely affected by the envisaged addition.

These substances may be selected variously by the person skilled in the art in order to prepare a composition which has the desired properties, for example, consistency or texture.

These additives may be present in the composition in a proportion from 0% to 99% (such as from 0.01% to 90%) relative to the total weight of the composition and further such as from 0.1% to 50% (if present), including all ranges and subranges therebetween.

Needless to say, the composition of the invention should be cosmetically or dermatologically acceptable, i.e., it should contain a non-toxic physiologically acceptable medium and should be able to be applied to the eyelashes of human beings.

According to preferred embodiments of the present invention, methods of treating, caring for and/or making up keratinous material such as skin, lips, eyes and eyelashes by applying compositions of the present invention to the keratinous material in an amount sufficient to treat, care for and/or make up the keratinous material are provided. Preferably, "making up" the keratin material includes applying at least one coloring agent to the keratin material in an amount sufficient to provide color to the keratin material.

According to yet other preferred embodiments, methods of enhancing the appearance of keratinous material by applying compositions of the present invention to the keratinous material in an amount sufficient to enhance the appearance of the keratinous material are provided.

According to yet other preferred embodiments, methods of volumizing and/or lengthening eyelashes and/or eyebrows by applying compositions of the present invention to the eyelashes and/or eyebrows in an amount sufficient to volumize and/or lengthen the appearance of the eyelashes and/or eyebrows are provided.

In accordance with the preceding preferred embodiments, the compositions of the present invention are applied topically to the desired area of the keratin material in an amount sufficient to treat, care for and/or make up the keratinous material, or to enhance the appearance of keratinous material or to volumize and/or lengthen eyelashes and/or eyebrows.

The compositions may be applied to the desired area as needed, preferably once or twice daily, more preferably once daily and then preferably allowed to dry before subjecting to contact such as with clothing or other objects (for example, a topcoat). Preferably, the composition is allowed to dry for about 1 minute or less, more preferably for about 45 seconds or less. The composition is preferably applied to the desired area that is dry or has been dried prior to application, or to which a basecoat has been previously applied.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

EXAMPLES

Example I—Sample Formulations

| PHASE | INGREDIENT | AMOUNT |
|---|---|---|
| | INVENTIVE COMPOSITION 1 | |
| A | WATER | 37.88 |
| A | GLYCOLS | 2.5 |
| A | PRESERVATIVES | 0.9 |
| A | VP/VA COPOLYMER | 3.5 |
| A | POLYQUATERNIUM-11 | 1.4 |
| A1 | AMINOMETHYL PROPANEDIOL | 1.32 |
| A2 | ALUMINUM STARCH OCTENYLSUCCINATE | 0.25 |
| A2 | COLORANTS | 12.5 |
| B | BIS-DIGLYCERYL POLYACYLADIPATE-2 | 3 |
| B | CETEARETH-33 | 2.3 |
| B | WAX | 16.9 |
| B | STEARIC ACID | 3.5 |
| B | PARAFFIN | 7.55 |
| B | GLYCERYL STEARATE | 0.75 |
| B | CETYL ALCOHOL | 2.4 |
| B | POLYBUTENE | 0.65 |
| B | VOLATILE HYDROCARBON OIL | 0.7 |
| C | ALCOHOL DENAT. | 2 |
| | INVENTIVE COMPOSITION 2 | |
| A | WATER | 33.83 |
| A | GLYCOLS | 2.5 |
| A | PRESERVATIVES | 0.9 |
| A | VP/VA COPOLYMER | 3.5 |
| A | POLYQUATERNIUM-11 | 1.4 |
| A1 | AMINOMETHYL PROPANEDIOL | 1.32 |
| A2 | ALUMINUM STARCH OCTENYLSUCCINATE | 0.25 |
| A2 | COLORANTS | 12.5 |
| B | BIS-DIGLYCERYL POLYACYLADIPATE-2 | 3 |
| B | CETEARETH-33 | 2.3 |
| B | WAX | 14.25 |
| B | STEARIC ACID | 3.5 |
| B | PARAFFIN | 6.25 |
| B | GLYCERYL STEARATE | 0.75 |
| B | CETYL ALCOHOL | 2.4 |
| B | POLYBUTENE | 0.65 |
| B | VOLATILE HYDROCARBON OIL | 0.7 |
| C | STYRENE/ACRYLATES/AMMONIUM METHACRYLATE COPOLYMER (and) SODIUM LAURETH SULFATE (and) CAPRYLYL GLYCOL | 10 |
| | Total | 100 |

Example II—Composition Preparation

The composition in Example I was prepared in the following manner:

Phase B ingredients were combined and heated to 80-85° C. Ingredients from all A phases (A, A1, A2 and A3) were charged into Phase B. The mixture was homogenized for 30 minutes at 80-85° C. Then, the mixture was cooled while using a sweep mixture. At 32° C., phase C was added and mixed until uniform for invention composition 1, and at 45° C. for invention composition 2. At 30° C., the batch was dropped.

Example III—Testing Protocols

Removal Analysis:

Experiments were run in triplicate. 30 strokes of product were applied to fake eyelashes in 10 stroke sets, spaced 2 minutes apart. Mascara compositions were allowed to dry for one hour. 1.5 ml of water was applied on a cotton pad and the cotton pad was placed on the fake lash sample. The fake lashes were held within the cotton pad for 10 seconds, at which point the cotton pad was dragged across the fake lash sample. This process was repeated with new cotton pads until the mascara composition was removed from the fake lash sample. The number of cotton pads used to remove the mascara composition from the fake lash sample indicated ease of removal, with fewer pads used indicating easier removal from lashes and, thus, better removability properties.

Flake Analysis:

Experiments were run in triplicate. 30 strokes of product were applied to fake eyelashes in 10 stroke sets, spaced 2 minutes apart. Mascara compositions were allowed to dry for one hour. Sample was held in place and brushed 10 times with a dry bristle mascara brush. Flakes were collected with tape and rated comparatively.

Texture Analysis:

Experiments were performed on a TA.XT Plus Texture Analyzer with a cylindrical TA-Delrin probe (10 mm diameter) in 6×2 cm stainless steel cups, filled with bulk at 25° C. Surface cut with stainless steel blade to ensure flat top surface. Settings: Test Mode: compression, Pre-test speed: 2 mm/sec, post-test speed: 2 mm/sec, test speed: 0.5 mm/sec, target mode: distance, distance: 5 mm, trigger force: auto, trigger force: 2 grams. After penetrating the sample the probe returned to its initial position. The curve generated is a plot of force (grams) as a function of time (seconds). When a 2 g surface trigger was attained, the probe proceeds to penetrate to a depth of 5 mm. At this point (maximum +ve force), the probe returns to its original position at constant speed (e.g. 2.0 mm/s). The maximum +ve force (hardness, grams) gave an indication of the softness of the sample. The smaller the peak force value, the softer sample. Data repeated in triplicate.

Example IV—Testing

The following compositions were prepared and tested for the identified properties:

|  | Control 1 (1) | Inv. 3 (36) | Inv. 4 (66) | Inv. 5 (73) | Inv. 6 (76) |
|---|---|---|---|---|---|
| Ingredient |  |  |  |  |  |
| AMINOMETHYL PROPANEDIOL |  | 1.32 | 1.32 | 1.32 | 1.32 |
| TRIETHANOLAMINE | 0.3 |  |  |  |  |
| Colorant | 7 | 12.5 | 12.5 | 12.5 | 12.5 |
| BIS-DIGLYCERYL POLYACYLADIPATE-2 | 3 | 3 | 3 | 3 | 3 |
| Volatile Hydrocarbon Oil | 3 | 0.7 | 0.7 | 0.7 | 0.7 |
| PARAFFIN | 3.5 | 7.55 | 7.55 | 4.93 | 6.25 |
| FATTY ALCOHOL |  | 2.4 | 2.4 | 1.22 | 2.4 |
| Wax | 8.5 | 16.9 | 16.9 | 11.57 | 14.25 |
| POLYQUATERNIUM-11 | 1.4 | 1.4 | 1.4 | 1.4 | 1.4 |
| ALUMINUM STARCH OCTENYLSUCCINATE | 0.25 | 0.25 | 0.25 | 0.25 | 0.25 |
| POLYBUTENE |  | 0.65 | 3 | 0.65 | 0.65 |
| ACRYLATES/C10-30 ALKYL ACRYLATE CROSSPOLYMER | 0.2 |  |  |  |  |
| VP/VA COPOLYMER | 3.5 | 3.5 | 3.5 | 3.5 | 3.5 |
| STYRENE/ACRYLATES/AMMONIUM METHACRYLATE COPOLYMER (and) SODIUM LAURETH SULFATE (and) CAPRYLYL GLYCOL |  |  | 20 | 7 | 10 |
| Preservatives | 0.9 | 0.9 | 0.9 | 0.9 | 0.9 |
| ALCOHOL DENAT. |  | 2 |  |  |  |
| WATER | 58.65 | 37.88 | 17.53 | 42.38 | 33.83 |
| Glycols | 2.5 | 2.5 | 2.5 | 2.5 | 2.5 |
| STEARIC ACID |  | 3.5 | 3.5 | 3.5 | 3.5 |
| GLYCERYL STEARATE | 5 | 0.75 | 0.75 | 0.38 | 0.75 |
| CETEARETH-33 | 2.3 | 2.3 | 2.3 | 2.3 | 2.3 |
| Characteristics |  |  |  |  |  |
| Production characteristic/DENSITY |  | >0.96 | >0.96 | >0.96 | >0.96 |
| Production characteristic/pH at 25° C. | 5.2-5.8 | 7-8 | 7-8 | 7-8 | 7-8 |
| Production characteristic/VISCOSITY rheomat at 25° C. |  | (M4) 13 to 80 UD | (M4) 13 to 80 UD | (M4) 13 to 80 UD | (M4) 13 to 80 UD |

| Presentation | POT | TUBE-PLUNGING APPLICATOR | TUBE-PLUNGING APPLICATOR | TUBE-PLUNGING APPLICATOR | TUBE-PLUNGING APPLICATOR |
|---|---|---|---|---|---|
| Sub-structure | OIL-IN-WATER EMULSION | OIL-IN-WATER EMULSION | OIL-IN-WATER EMULSION | OIL-IN-WATER EMULSION | OIL-IN-WATER EMULSION |
| Structure | EMULSION | EMULSION | EMULSION | EMULSION | EMULSION |
| Rinse-Off | No | No | No | No | No |
| Consumer category | Hair Cream | Mascara washable | Mascara washable | Mascara washable | Mascara washable |
| Physical form | Cream/Paste/Gel | Cream/Paste/Gel | Cream/Paste/Gel | Cream/Paste/Gel | Cream/Paste/Gel |

Example 5—Testing

Comparative compositions were prepared corresponding to the invention composition in Example I but which lacked (1) VP/VA; or (2) polyquaternium-11 and compared with the invention composition.

Removal:

The removal test demonstrated that the invention compositions resulted in easier removal as compared to the comparative compositions which did not contain all required ingredients. Ease of removal was graded on a scale 1 to 5 (the higher the number, the more difficult it was to remove):
 VP/VA only=3;
 Polyquaternium-11 only=4;
 VP/VA+Polyquaternium-11=2.5,
 Invention composition=1.

Flake:

The flake test demonstrated that the invention compositions resulted in less flaking than the comparative compositions. The flake rating was on a scale 1 to 5 (the higher the number, the higher amount of flakes):
 VP/VA only=3;
 Polyquaternium-11 only=3.5;
 VP/VA+Polyquaternium-11=3.5,
 Invention composition=2.

Texture:

The texture test demonstrated that by invention compositions resulted in better texture as compared to compositions which did not contain all required ingredients. The consistency characterized by complex modulus G* (measured by rheology) increased in an order of magnitude with invention compositions. Invention compositions had RMS G*=4.27*E4 as compared to a composition lacking VP/VA and polyquaternium-11 which had RMS G*=1.35*E5. In other words, the comparative composition became very thick, and it didn't appear to be creamy any longer and could not be applied easily.

What is claimed is:

1. A composition comprising water, at least one polyelectrolytic compound, at least one film-forming agent which is a copolymer, at least one high melting point hydrocarbon wax, at least one low melting point hydrocarbon wax, at least one volumizing agent, and an emulsification system comprising at least one low HLB emulsifier and at least one high HLB emulsifier, wherein the composition is an eyelash coating composition and wherein the composition is free of polyethylene wax and of film-forming agent resulting from copolymerization of vinyl monomer(s) and amide(s).

2. The composition of claim 1, wherein the polyelectrolytic compound comprises at least one quaternary group.

3. The composition of claim 1, wherein the polyelectrolytic compound is selected from the group consisting of Polyquaternium 2, Polyquaternium 4, Polyquaternium 5, Polyquaternium 6, Polyquaternium 7, Polyquaternium 8, Polyquaternium 10, Polyquaternium 11, Polyquaternium 17, Polyquaternium 18, Polyquaternium 22, Polyquaternium 24, Polyquaternium 27, Polyquaternium 39, Polyquaternium 44, Polyquaternium 53, Polyquaternium 67, and mixtures thereof.

4. The composition of claim 1, wherein the polyelectrolytic compound is polyquaternium-11.

5. The composition of claim 1, wherein the polyelectrolytic compound is present in an amount from about 0.1% to about 1% based on the total weight of the composition.

6. The composition of claim 4, wherein the polyelectrolytic compound is present in an amount from about 0.1% to about 1% based on the total weight of the composition.

7. The composition of claim 1, wherein the composition is a mascara.

8. The composition of claim 1, further comprising at least one colorant.

9. The composition of claim 1, in the form of an oil-in-water emulsion.

10. The composition of claim 1, wherein the low HLB emulsifier(s) and the high HLB emulsifier(s) are present in a weight ratio of from 0.1 to 10.

11. The composition of claim 5, wherein the low HLB emulsifier(s) and the high HLB emulsifier(s) are present in a weight ratio of from 0.1 to 10.

12. The composition of claim 1, wherein the low melting point wax(es) and high melting point wax(es) are present in a weight ratio of from 0.5 to 40.

13. The composition of claim 11, wherein the low melting point wax(es) and high melting point wax(es) are present in a weight ratio of from 0.5 to 40.

14. The composition of claim 1, wherein the polyelectrolytic compound(s) and film-forming polymer(s) are present in a weight ratio of from 0.55:0.5 polyelectrolytic compound(s) to 10:40 film forming polymer(s).

15. The composition of claim 13, wherein the polyelectrolytic compound(s) and film-forming polymer(s) are present in a weight ratio of from 0.55:0.5 polyelectrolytic compound(s) to 10:40 film forming polymer(s).

16. The composition of claim 1, wherein the composition is a volumizing eyelash coating composition.

17. The composition of claim 1, wherein the low HLB emulsifier(s) and/or the high HLB emulsifier(s) are ethoxylated fatty alcohols containing from 9 to 250 oxyethylenated groups.

18. An oil-in-water emulsion comprising water, from about 0.1% to about 1% based on the total weight of the composition of polyquaternium-11, at least one copolymer of vinylpyrrolidone and vinyl acetate, at least one styrene/acrylates/ammonium methacrylate copolymer, at least one high melting point hydrocarbon wax, at least one low melting point hydrocarbon wax, at least one volumizing agent, and an emulsification system comprising at least one low HLB emulsifier and at least one high HLB emulsifier, wherein the composition is an eyelash coating composition and wherein the composition is free of polyethylene wax and of film-forming agent resulting from copolymerization of vinyl monomer(s) and amide(s).

19. The composition of claim 1, wherein the at least one film forming agent is selected from the group consisting of styrene/acrylates/ammonium methacrylate copolymers, copolymers of vinylpyrrolidone and vinyl acetate, and mixtures thereof.

20. The composition of claim 1, wherein at least one high melting point hydrocarbon wax is rice bran wax and the at least one low melting point hydrocarbon wax is paraffin wax.

21. The composition of claim 1, wherein the at least one film forming agent is at least one film-forming agent resulting from copolymerization of (1) vinyl monomer(s), and (2) acid monomer(s) and/or ester(s) thereof.

* * * * *